United States Patent [19]

McCollough et al.

[11] 4,275,166

[45] Jun. 23, 1981

[54] PROCESS FOR THE RECOVERY OF INTRACELLULAR ENZYME

[75] Inventors: George T. McCollough, Penfield; Theodore W. Esders, Webster; Shirley Y. Lynn, Rochester, all of N.Y.

[73] Assignee: Eastman Kodak Company, Rochester, N.Y.

[21] Appl. No.: 91,217

[22] Filed: Nov. 5, 1979

[51] Int. Cl.$^3$ .............................................. C12N 9/78
[52] U.S. Cl. .................................... 435/227; 435/259; 435/816; 435/850
[58] Field of Search ....................... 435/227, 259, 816

[56] References Cited

U.S. PATENT DOCUMENTS

| | | | |
|---|---|---|---|
| 3,597,323 | 8/1971 | Roberts | 435/816 X |
| 4,087,329 | 5/1978 | Terada et al. | 435/227 |
| 4,134,793 | 1/1979 | Terada et al. | 435/18 |

Primary Examiner—Lionel M. Shapiro
Attorney, Agent, or Firm—J. Jeffrey Hawley

[57] ABSTRACT

A process for the recovery of an intracellular enzyme from an aerobic soil microorganism is disclosed. The recovery method is carried out by (a) forming an aqueous suspension of microbial cells containing the desired intracellular enzyme, (b) disrupting the microbial cells in the suspension to release the enzyme from the cells, and (c) before, during, or after step (b) and prior to removal of disrupted microbial cells and other cellular components, introducing a water-miscible organic solvent into the suspension to form a mixture of the organic solvent and the enzyme-containing suspension.

The desired enzyme is retained in the liquid phase of the mixture formed in step (c) while undesired cellular components such as other microbial cell proteins precipitate therefrom.

12 Claims, No Drawings

PROCESS FOR THE RECOVERY OF INTRACELLULAR ENZYME

FIELD OF THE INVENTION

This invention relates to a process for the efficient recovery of enzyme produced intracellularly by an aerobic microorganism. The invention is particularly useful for obtaining excellent yields and enhanced stabilization of an intracellular creatinine iminohydrolase enzyme during the recovery thereof from an aerobic soil microorganism.

BACKGROUND OF THE INVENTION AND RELATED APPLICATIONS

Creatinine iminohydrolase, sometimes referred to as creatinine desimidase, is an enzyme which specifically catalyzes the hydrolysis of creatinine to ammonia. The aerobic soil microorganism ATCC #31546 represents a new microbial source of creatinine iminohydrolase. Creatinine iminohydrolase from this source is particularly useful because it is substantially free from urease activity, urease being a highly undesirable interferent for creatinine assays conducted on aqueous liquids containing both creatinine and urea. Accordingly, urease-free creatinine iminohydrolase together with an ammonia detector can provide a quantitative assay composition for the determination of creatinine contained in aqueous liquids, e.g., serum. The urease-free creatinine iminohydrolase from the aerobic soil microorganism ATCC #31546 is described in greater detail in Goodhue, Esders, and Masurekar copending U.S. patent application Ser. No. 91,218 filed concurrently herewith and entitled "Creatinine Iminohydrolase Free From Urease Activity".

The above-referenced urease-free creatinine iminohydrolase is produced intracellularly by the microorganism and must be extracted therefrom following growth of the microbial cells. A useful fermentation process for growing microbial cells of ATCC #31546 containing substantial quantities of the desired urease-free creatinine iminohydrolase enzyme is described in Masurekar, copending U.S. patent application Ser. No. 91,216 filed concurrently herewith and entitled "Process and Nutrient Medium For Growing Microorganisms".

Recovery of the intracellularly produced creatinine iminohydrolase enzyme referenced hereinabove is carried out by known techniques wherein the cells are disrupted to release the enzyme, followed, if desired, by partial purification of the enzyme. Well-known cell disruption techniques include sonication, grinding, and the like. Partial purification is typically performed by separating the desired enzyme from the microbial cell debris such as by centrifugation, filtration, or the like followed by organic solvent fractional precipitation to separate the desired enzyme from other microbial cell protein.

The aforementioned disruption and partial purification procedure typically employs a sequence of individual process steps including cell disruption and separation of the desired intracellular enzyme from microbial cell debris, followed by organic solvent fractional precipitation. For example, the aforementioned sequence of individual process steps is disclosed in U.S. Pat. Nos. 4,087,329 and 4,134,793 which describe the recovery of creatinine desimidase (another name for creatinine iminohydrolase) from various aerobic microorganisms.

This sequential procedure, however, extracts only a portion of the enzyme from the microbial cells. In addition, the individual process step of separating the desired enzyme from microbial cell debris requires extensive centrifugation or filtration equipment and time when carried out on a large-scale production basis.

Moreover, creatinine iminohydrolase produced intracellularly by an aerobic soil microorganism, when recovered from the microorganism by the aforementioned sequential procedure, exhibits a problem of enzyme instability. That is, the enzyme, during recovery from the microbial cells, often exhibits a marked decrease in activity. This same enzyme instability problem may also be exhibited by other intracellular enzymes.

Accordingly, a more efficient process for recovering enzymes produced intracellularly by aerobic microorganisms would clearly be a useful contribution to the art. Such a process would be particularly desirable for use with intracellular enzymes such as the above-referenced urease-free creatinine iminohydrolase if it also could stabilize the enzyme during the process and improve the yield of the desired enzyme.

SUMMARY OF THE INVENTION

The present invention advantageously provides an efficient method for recovering enzyme produced intracellularly by an aerobic microorganism. In the case of intracellular enzymes such as the above-referenced creatinine iminohydrolase, the present invention also provides the unexpected benefits of increasing yields and stabilizing the enzyme during the recovery process.

The recovery method of the invention comprises:

(a) forming an aqueous suspension of microbial cells of an aerobic microorganism;

(b) disrupting the microbial cells in the suspension to release the enzyme from the cells; and (c) before, during, or after step (b) and prior to removal of disrupted microbial cells and other cellular components, introducing a water-miscible organic solvent into the suspension to form a mixture of the organic solvent and the enzyme-containing suspension, the mixture being effective to retain the desired enzyme in the liquid phase thereof while undesired cellular components such as other microbial cell proteins precipitate therefrom.

An especially preferred embodiment of the present recovery method comprises the additional steps of:

(d) separating the enzyme-containing liquid phase of step (c) from the precipitate and the disrupted microbial cells, for example, by centrifugation or filtration, and (e) introducing additional water-miscible organic solvent into the separated liquid phase of step (d) to precipitate the desired enzyme therefrom.

The resultant enzyme-containing precipitate can thereafter be separated, admixed with an aqueous buffer composition to place the enzyme in a more useful aqueous preparation substantially free of the organic solvent, and/or subjected to further purification if necessary or desired. The organic solvent-free aqueous enzyme preparation is useful directly or as a freeze-dried powder of the desired enzyme.

In a preferred embodiment, steps (a) and (b) of the present recovery method are performed by thawing frozen cells containing the desired intracellularly produced enzyme in the presence of an aqueous liquid subjected to physical agitation whereby the thawed cells are suspended in the aqueous liquid and enzyme is released from the cells into the suspension. The physical agitation should be sufficient to maintain the resulting suspension in a fluid state to avoid formation of a highly viscous suspension.

The present invention has been found particularly helpful to stabilize intracellular creatinine iminohydrolase during the recovery thereof from aerobic soil microorganisms such as ATCC #31546. In addition, the yield of creatinine iminohydrolase recovered from ATCC #31546 by the present method is at least 25%, preferably more than 100%, greater than that recovered by the known sequence of individual process steps described in the Background of the Invention.

DESCRIPTION OF THE PREFERRED EMBODIMENTS

The present recovery method advantageously provides important features and advantages. For example, conventional recovery processes require an individual separation step, such as a centrifugation step, to separate the desired intracellular enzyme from the disrupted microbial cells (as well as other insoluble cell debris) prior to introduction of a water-miscible organic solvent to carry out enzyme purification. In the present method, however, introduction of the desired water-miscible organic solvent into the aqueous suspension containing the desired intracellular enzyme is carried out prior to removal of the disrupted microbial cells, thereby eliminating a separate step for removal of these materials. Thus, the present method effectively eliminates an entire separation operation and thereby reduces enzyme production time and equipment.

A further advantage of the present method is the improved yield of intracellular enzyme which can be achieved, for example, in the case of enzymes such as the urease-free creatinine iminohydrolase derived from the aerobic soil microorganism #31546 referenced hereinabove. This improved yield results from the increase in the percentage of enzyme released from the microorganism and from the stabilization of the enzyme against subsequent loss of activity during the recovery process. The specific mechanism(s) whereby the foregoing results are obtained is not completely understood. Whatever the mechanism(s), however, these results are brought about by the introduction of the water-miscible organic solvent in step (c) of the present method prior to the removal of the disrupted microbial cells and other cellular components produced during step (b).

The microorganism identified herein as ATCC #31546 has received this designation based on its deposit with the American Type Culture Collection, Rockville, Md. 20852, USA. This microorganism has tentatively been assigned to the genus Flavobacterium and given the species name *filamentosum*.

The present invention, as stated hereinabove, is directed to the recovery of an intracellularly produced enzyme from an aerobic microorganism. The growth of the microbial cells containing therein the desired enzyme is not a principal concern of the present invention and is carried out prior to instituting the present method. A variety of microorganism growth (fermentation) procedures as well as nutrient media are known in the art for supporting and enhancing cell growth and intracellular enzyme production by aerobic microorganisms. These procedures and media, of course, vary in large part depending upon the particular microorganism to be grown as well as the specific enzyme which is desired to be produced within the cells of the microorganism during growth thereof. Accordingly, extended description of such procedures and nutrient media are not material to the present invention and one should instead refer to the literature relevant to the particular microorganism and the specific enzyme to be generated therein.

As to a preferred embodiment of the invention wherein urease-free creatinine iminohydrolase is recovered from the aerobic soil microorganism ATCC #31546, reference is made to the previously mentioned Goodhue, Esders, and Masurekar U.S. patent application and the previously mentioned Masurekar U.S. patent application appearing in the Background of the Invention for information as to further description of this microorganism, preferred nutrient media, and preferred procedures for cell growth of and enzyme production by this microorganism. These applications are expressly incorporated by reference herein.

Having produced cells containing the desired enzyme in a suitable nutrient medium, the cells are separated from the nutrient medium so that recovery of the desired intracellular enzyme can be initiated. Typically, this is carried out by centrifuging or filtering the nutrient medium containing the microbial cells thereby separating and collecting the cells from the medium in which they were grown. Recovery of the enzyme from the collected cells is initiated immediately; or the collected cells can conveniently be stored under reduced temperature conditions until the enzyme recovery method is to be performed. For example, in the case of a preferred embodiment of the present method relating to extraction of urease-free creatinine iminohydrolase from the aerobic soil microorganism ATCC #31546, cells of this microorganism containing the desired enzyme are frozen whereby the desired enzyme is essentially maintained without substantial loss of activity within the frozen microbial cells.

Once the microbial cells containing the desired enzyme are collected, the present recovery method can begin. The present method is initiated in steps (a) and (b) as described above by disrupting the cells while they are suspended in an aqueous liquid to release the desired enzyme from the cells into the suspension. The conditions under which these steps are carried out will vary widely depending upon the particular enzyme and microbial cells involved. Thus, one must choose pH and temperature conditions for these steps which do not adversely interfere with the desired enzyme and its level of activity. For example, in the case of the preferred microbial cells of ATCC #31546, the cells are suspended and the desired urease-free creatinine iminohydrolase is released in steps (a) and (b) of the present method at a temperature within the range of from about 4° to 37° C., preferably about 20° to 25° C., and at a pH within the range of from about 5.0 to 10, preferably about 7 to 7.5. However, for microorganisms and enzymes which are not adversely affected by higher or lower pH and temperature values, one can readily employ conditions outside the foregoing ranges.

The quantity of microbial cells in the aqueous suspension in which cell disruption is performed is variable depending, in part, not only upon the particular cells and desired enzyme preparation obtained therefrom but also on the specific cell disruption procedure to be employed. A partial listing of representative cell disruption procedures includes sonication treatment, such as continuous-flow sonication of the cells suspended in an aqueous media; and grinding such as by subjecting an aqueous suspension of the microbial cells to grinding in a DYNOMILL ® (available from the Willy A. Bachofen Maschinenfabrik Company, Basel, Switzerland). Typically, the solids content of the aqueous suspension in which cell disruption is performed is within the range of from about 5 to 40 wt% based on the wet weight of the microbial cells contained in the aqueous suspension.

An especially preferred technique for suspending and disrupting cells, particularly cells containing urease-free creatinine iminohydrolase, is accomplished by suspending frozen cells of the microorganism in the aqueous liquid under room temperature conditions (approximately 22° C.) while subjecting the suspension to physical agitation such as by vigorous stirring. In this manner, the desired urease-free creatinine iminohydrolase enzyme is effectively released into the aqueous suspension, and the suspension is maintained in a fluid state. This prevents the suspension from forming a highly viscous suspension which results in little or no release of enzyme. When cell disruption and enzyme release is carried out by the foregoing technique of thawing frozen cells coupled with physical agitation, effective levels of physical agitation can conveniently be achieved, for example, in a 200-liter tank, 56 cm in diameter, by employing a 9.4 cm propeller rotated at 400 rpm.

The specific method of agitating a particular aqueous suspension as well as the time of agitation will vary widely depending upon the volume of the suspension, the quantity and type of cells therein, and the equipment by which the agitation is carried out. These parameters are readily determined by those of ordinary skill in the art for a specific enzyme. In the case of the preferred aerobic soil microorganism ATCC #31546, cell disruption in the above-described 200-liter tank operating at 400 rpm is effectively carried out using a 20-hour agitation time.

Step (c) of the present method is carried out by introducing a water-miscible organic solvent into the aqueous cell suspension. Step (c) is initiated before, during or after step (b). In accord with the present method, as explained above, introduction of this organic solvent is begun in step (c) without prior separation of disrupted microbial cells and other cellular components released into the aqueous suspension during step (b). The particular organic solvent selected should be a water-miscible solvent which forms a water-solvent mixture effective to precipitate a substantial amount of undesired cellular components such as other microbial cell proteins while retaining the desired enzyme dissolved or suspended in the liquid phase (supernatant) of the water-solvent mixture. Accordingly, the temperature conditions, the particular water-miscible solvent, and the solvent-water ratio selected for step (c) will depend, in large part, on the solubility characteristics of the particular microbial cell waste components as well as on the solubility characteristics of the desired enzyme. In the case of the preferred urease-free creatinine iminohydrolase derived from the aerobic soil microorganism ATCC #31546, a partial listing of useful water-miscible organic solvents includes propanol, for example, n-propanol and isopropanol, t-butanol, ethanol, acetone, and the like, n-propanol being preferred.

At the conclusion of step (c) of the present method, the desired intracellular enzyme has been removed from the microbial cells in which it was produced and separated into the liquid phase of an organic solvent-water mixture, such liquid phase being free from the bulk of disrupted microbial cells and other cellular components. The desired enzyme has therefore been recovered, although it remains in crude form associated in the organic solvent-water mixture with other microbial cell proteins and cell components which are as soluble or more soluble than the microbial cell protein constituting the desired enzyme. For this reason, further enzyme purification is often desired.

In addition, because most enzymes are used in aqueous environments, placing the intracellular enzyme into a form or medium free of the organic solvent is highly desirable. Accordingly, steps (d) and (e) of the present method which place the desired enzyme in a more purified form easily separable from the organic solvent, although optional, are considered particularly useful.

In steps (d) and (e) the supernatant containing the desired intracellular enzyme is separated from the precipitate containing the disrupted cells and undesired microbial cell proteins, and then additional water-miscible organic solvent is introduced into the supernatant containing the desired enzyme to precipitate the desired enzyme therefrom. The combined effect of steps (c), (d) and (e) amounts to an organic solvent fractional precipitation procedure, the additional organic solvent added in step (e) providing a sufficient organic solvent fraction in the water-organic solvent mixture to cause precipitation of the desired intracellular enzyme.

In step (d), the separation of the enzyme-containing supernatant obtained in previous step (c) is conveniently carried out by known separation procedures such as centrifugation or filtration, filtration being carried out, for example, using a rotary vacuum filter, filter press, etc.

The water-miscible organic solvent introduced in step (e) into the separated liquid phase obtained from previous step (d) (that is, the step (d) supernatant) to effect precipitation of the desired intracellular enzyme is typically (although not necessarily) the same water-miscible organic solvent introduced into the enzyme-containing aqueous suspension in step (c) of the present method. The selection and the amount of the specific water-miscible organic solvent employed in step (e) depends in large part upon the particular solubility characteristics and the conditions (for example, temperature conditions) under which the solvent is introduced into the step (d) supernatant. When the present method is carried out employing the combination of steps (c), (d) and (e), the selection of the water-miscible organic solvent in step (c) typically must take into account the function that the solvent is to perform in step (e) as well as in step (c). In accord with a preferred embodiment of the present method, the water-miscible organic solvent employed in steps (c) and (e) is identical and is selected such that the addition of a first quantity of the organic solvent in step (c) is effective to precipitate a large portion of the undesired contaminants while the desired intracellular enzyme protein is retained in a liquid phase supernatant. Thereafter, in step (e) the desired enzyme contained in this supernatant is precipitated therefrom by introduction of a second quantity of the solvent into this supernatant. Organic solvents useful in step (e) include any organic solvent exhibiting the foregoing performance characteristics. In the case of the preferred urease-free creatinine iminohydrolase derived from the aerobic soil microorganism ATCC #31546 referred to hereinabove, a partial listing of useful water-miscible organic solvents includes many of the same solvents previously noted for use in step (c), such as n-propanol, isopropanol, t-butanol, acetone, and the like. Other water-miscible organic solvents are also useful for the preferred microorganism, and, of course, still other organic solvents are useful for microorganisms other than the aforementioned ATCC #31546.

The temperature conditions under which steps (c), (d) and (e) of the present method are carried out are variable and will depend, in large part, on the particular microorganism and the specific intracellular enzyme to be recovered therefrom. Typically, it is desirable to carry out steps (c), (d) and (e) at temperatures within the range of from about $-10°$ to $37°$ C., preferably about $2°$ to $5°$ C. This is readily accomplished by carrying out steps (c), (d) and (e), for example, in jacketed containers through which a glycol coolant is circulated. Of course, for those aerobic microorganisms and intracellular enzymes recovered therefrom which are not adversely affected by higher temperatures, temperatures above the foregoing level are readily employed.

Similarly, the pH conditions under which steps (c), (d) and (e), are carried out are variable and will depend in large part upon the particular microorganism and specific intracellular enzyme to be recovered therefrom. Typically, these steps are carried out under pH conditions extending from about 5.0 to about 10.0, preferably 6.0 to 8.0. However, for microorganisms and enzymes which are not adversely affected by lower or higher pH levels than those noted above, one can readily employ pH conditions outside of the foregoing ranges, if desired.

Having obtained a more purified form of the desired intracellular enzyme in step (e) of the present method as a precipitate, one can, if desired, freeze-dry this enzyme-containing precipitate to obtain a powder form of the enzyme. Preferably, however, one subjects the enzyme to further purification such as by admixing the precipitate in an aqueous solution buffered to a pH level effective to maintain the enzyme activity. This will effect separation of any undesired water-insoluble contamination, such as undesired microbial protein, which is still associated with the desired intracellular enzyme, the enzyme being dissolved in the buffer solution. Accordingly, following step (e), the enzyme-containing precipitate is typically separated from the liquid phase such as by filtration or centrifugation as described above, and admixed in an aqueous buffer solution. The desired intracellular enzyme dissolves in the aqueous buffer while the undesired water-insoluble contaminants remain as a precipitate. The resultant supernatant containing the desired enzyme is saved and the precipitate is discarded. If desired, however, the precipitate is collected and admixed in additional aqueous buffer to remove any further residue of the desired soluble intracellular enzyme still associated therewith while the undesired water-insoluble contaminant remains as a precipitate. Thereafter, the enzyme-containing supernatants from the aqueous buffer solutions is combined to form a final aqueous enzyme preparation ready for use. Of course, still further purification procedures such as various chromatographic procedures can be employed if desired. The final aqueous enzyme preparation is then used directly, concentrated, or this preparation is freeze-dried to obtain the desired enzyme in powder form.

The present recovery method can be carried out with advantageous effect on various aerobic microorganisms to obtain intracellular enzymes produced by these microorganisms. As noted above, the present invention has been found especially useful for the aerobic soil microorganism ATCC #31546 to recover urease-free creatinine iminohydrolase.

The following non-limiting examples are provided to further illustrate the invention.

In the examples, the following materials and procedures were employed:

Materials

Nicotinamide adenine dinucleotide phosphate, reduced form (NADPH); L-glutamic dehydrogenase (GDH); tris(hydroxymethyl)aminomethane (tris); N,N-bis(2-hydroxyethyl)-glycine (bicine); egg white lysozyme, ribonuclease and deoxyribonuclease from bovine pancreas all were supplied by Sigma Chemical Co., St. Louis, Mo. Other organic chemicals were obtained from Eastman Organic Chemicals, Eastman Kodak Company, Rochester, N.Y. Deionized water was used throughout.

Procedures

1. Use of Lysozyme for Fermentation Assay

Lysozyme treatment of microbial cells referred to in the Examples below results in breakage of the cells with subsequent release of the enzyme. Lysozyme treatment was carried out by the following procedure:

A sample of harvested aerobic soil microorganism ATCC #31546 cells was taken from 110 liters of aqueous nutrient medium in a 150-liter fermentor. The composition of the aqueous nutrient medium in the fermentor, on a per liter basis, was as follows:

| | |
|---|---|
| fumaric acid | 10 g |
| creatinine | 5 g |
| $K_2HPO_4$ | 5 g |
| yeast extract | 1 g |
| Polyglycol P-2000* | 0.1 g |
| $MgSO_4 . 7H_2O$ | 0.12 g |
| $CaCl_2 . 2H_2O$ | 0.00076 g |
| $FeSO_4 . 7H_2O$ | 0.028 g |
| $MnSO_4 . H_2O$ | 0.017 g |
| NaCl | 0.006 g |
| $NaMoO_4 . 2H_2O$ | 0.001 g |
| $Z_nSO_4 . 7H_2O$ | 0.0006 g |
| KOH sufficient to adjust pH to 6.7. | |

*(Tradename for a polyglycol antifoam agent sold by Dow Chemical Co, Midland, Ml.)

The cell suspension was diluted in 0.05 M tris buffer, pH 8.5, and $10^{-3}$ M (ethylenedinitrilo)tetraacetic acid, dipotassium salt ($K_2$EDTA) to an optical density at 660 nm of less than one. To this suspension, 1.8 ml of 0.05 M tris buffer and 0.2 ml of lysozyme solution were added. The lysozyme solution contained per ml of deionized water: 5.0 mg of lysozyme, 1 mg bovine pancreatic deoxyribonuclease, and 1 mg bovine pancreatic ribonuclease. The suspension was shaken in a water bath at 37° C. for 20 minutes. The cell debris was removed by centrifugation at 15,000 rpm in a refrigerated centrifuge for 15 minutes, and the enzyme activity of the supernatant was determined by the method described in Procedure 2 below. The total activity of the harvested ATCC #31546 cells was calculated by projecting the value based on this small-scale assay to the entire contents of the fermentor.

2. Assay of Creatinine Iminohydrolase

To determine the creatinine iminohydrolase activity described in the Examples below, a L-glutamic dehydrogenase, "GDH", assay method was employed. In this GDH assay method, production of ammonia from creatinine, which represents the activity of a creatinine iminohydrolase enzyme preparation, was measured using NADPH (nicotinamide-adenine dinucleotide phosphate, reduced form) in a GDH-catalyzed reaction as follows:

Creatinine is catalytically hydrolyzed to ammonia by the enzymatic activity of an unknown creatinine iminohydrolase enzyme sample, and the resultant ammonia reacts with the reagent α-ketoglutaric acid in the presence of GDH as catalyst to produce glutamic acid. The latter reaction catalyzed by GDH concomitantly converts NADPH to NADP, the disappearance of the NADPH absorption peak at 340 nm providing the spectroscopically detectable means for monitoring the assay. That is, the NADPH disappearance rate measures the rate of glutamic acid production which, in turn, measures the rate of ammonia production. The reaction mixture employed in the GDH assay method contained, in a total volume of one milliliter of 0.1 M N,N-bis(2-hydroxyethyl)-glycine-KOH buffer solution having a pH of 7.5: 0.4 mg (ethylenedinitrilo) tetraacetic acid, disodium salt ($Na_2EDTA$), 1.6 mg α-ketoglutaric acid, 0.24 mg NADPH, 15 units GDH (ammonia free), and 4.52 mg creatinine. One unit of L-glutamic dehydrogenase is defined as that amount of enzyme which catalyzes the reduction of 1 micromole of α-ketoglutarate to glutamate per minute at pH 7.6 and 37° C. Reaction was initiated in the above-noted reaction mixture by addition of a small sample (about 2–10 milliunits) of the desired creatinine iminohydrolase enzyme preparation after equilibration of the reaction mixture at 37° C. Creatinine iminohydrolase activity was calculated by measuring the rate of NADPH disappearance at 340 nm (the molar extinction coefficient of NADPH at 340 nm being $6.22 \times 10^3$) in a Beckman Model 25 spectophotometer. One unit of enzyme activity was defined as that amount of enzyme necessary to catalyze the conversion of 1 micromole of creatinine to 1 micromole of ammonia per minute under the above-noted GDH assay reaction conditions.

3. Stirring Conditions

A 200-liter tank, 56 cm in diameter having a 9.4 cm propeller rotated at 400 rpm was used to vigorously stir the cell suspensions described in the Examples below.

EXAMPLE 1

Recovery of Intracellular Enzyme

Cells of the aerobic soil microorganism ATCC #31546 were collected by centrifugation from a fermentation medium as described in Procedure 1 above and frozen at −15° C. for between 4 to 22 days. The frozen cells were placed in a 200-liter tank containing 70 liters of 0.1 M tris phosphate buffer, pH 7.5, and stirred vigorously at room temperature for 20 hours. The cell suspension in the tank was quickly chilled to 4° C., and 77 liters of n-propanol at 4° C. was added. The alcohol was pumped into the vigorously mixing suspension at a rate of 30 liters/hour. Upon completion of the alcohol addition, the suspension was pumped through an 8-liter capacity solids-holding centrifuge (Cepa type sold by Carl Padberg Gmbh.) at a rate of 15 liters/hour. The supernatant containing the desired enzyme was stored at 4° C. and the pellet was discarded. A second addition of n-propanol (38.5 liters) was made to the supernatant at a rate of 30 liters/hour at 4° C.; vigorous mixing was maintained throughout the addition. Upon completion, the water-propanol suspension was pumped through a 2-liter capacity solids-holding centrifuge (Cepa type 41G sold by Carl Padberg Gmbh.) at a rate of 30 liters/hour. The supernatant was discarded. The pellet containing the desired creatinine iminohydrolase enzyme was re-suspended in 3.5 liters of 0.01 M tris phosphate buffer, pH 7.5, and stirred overnight at 4° C. Solids in the suspension were separated by the 2-liter centrifuge (Cepa type 41G), both the supernatant and the pellet were collected. The supernatant contained most of the desired enzyme. The pellet was re-suspended in tris phosphate buffer as before and centrifugation was carried out again. The second supernatant containing some enzyme was then combined with the first supernatant, and the combined supernatant was lyophilized on a Virtis model 50-SRC-5 freeze dryer (sold by the Virtis Co., Gardiner, N.Y.) for 48 hours. 126 g of a free-flowing, cream-colored, enzyme-containing powder was recovered.

EXAMPLE 2

Release of Creatinine Iminohydrolase From A Microbial Source

Creatinine iminohydrolase was released from the aerobic soil microorganism ATCC #31546 by vigorous stirring. Enzyme release was further enhanced by addition of n-propanol directly to the cell suspension as shown in this Example.

A. Enzyme Release by Vigorous Stirring

Frozen cells were thawed and suspended in 10 liters of 0.1 M tris phosphate buffer (pH 7.5) per kg of cell wet weight. (A fermentation assay as described in Procedure 1 above was conducted on a sample of these cells before they were frozen). The suspension was then vigorously stirred as described in Procedure 3 above at 22° C. for 20 hours. An aliquot was removed from the suspension, centrifuged, and enzyme activity of the supernatant was measured as described in Procedure 2 above. As shown in Table I (Column 1), a high percentage of enzyme based on the fermentation assay was released by vigorous stirring.

B. Enzyme Release Enhanced by Addition of n-Propanol

To the remaining cell suspension of A above, an equal volume of n-propanol was directly added. The 50% propanol supernatant was separated by centrifugation. The enzyme activity of the supernatant was determined as described in Procedure 2 above. As shown in Table I (Column 2), vigorous stirring and direct addition of propanol provided a higher percentage of enzyme released from the cells than the use of vigorous stirring alone. This procedure was repeated six times.

TABLE I

| Batch | Enzyme Released by Vigorous Stirring* | Enzyme Released by Vigorous Stirring and Direct Addition of Propanol to the Cell Suspension* | % Increase** |
|---|---|---|---|
| 1 | 89 | 108 | 19 |
| 2 | 77 | 91 | 14 |
| 3 | 82 | 93 | 11 |
| 4 | 102 | 119 | 17 |
| 5 | 78 | 96 | 18 |
| 6 | 91 | 113 | 22 |
| Average | 86 | 103 | 17 |

*% of fermentation assay conducted according to Procedure 1
**Column 2 minus Column 1

EXAMPLE 3

Enhanced Overall Enzyme Yield

Enzyme yield obtained by direct addition of n-propanol to the cell suspension (procedure of the present invention) was compared to a procedure in which addition of n-propanol was made following centrifugation of the cell suspension to remove cell debris.

In the method of the invention, 7 kg of ATCC #31546 microbial cells were collected by centrifugation from the fermentation medium in Procedure 1 above. A small sampling of cells was broken using lysozyme solution as described in Procedure 1, and the enzyme activity was measured by the GDH method described in Procedure 2 above. This level is projected to equal the initial enzyme activity (Item 1 in Table II). The remaining cells were frozen at −15° C. for between 4 to 22 days. The frozen cells then were placed in a 200-liter tank containing 70 liters of 0.1 M tris phosphate buffer, pH 7.5, and stirred vigorously at room temperature for 20 hours. A 30-ml sample was removed, centrifuged, and enzyme activity of the supernatant was assayed as in Procedure 2 above (Item 2 of Table II). The remaining cell suspension was processed (Items 3 and 4 of Table II) according to the procedure of the present invention as described in Example 1 above, except that the pellet containing the desired enzyme was admixed in one volume of aqueous buffer to separate insoluble components and this aqueous buffer treatment was not repeated. Results of this procedure are shown in Table II.

TABLE II

Summary of a Typical Large-Scale Purification Process (Direct Addition of Alcohol to the Cell Suspension)

| | Purification Step | Total Units | Yield % |
|---|---|---|---|
| 1. | An aliquot of the 7 kg of cells from the fermentation treated with lysozyme solution (initial activity) | 157,500 | |
| 2. | Enzyme released by stirring at 22° C. for 20 hours | 142,800 | 91 |
| 3. | Direct addition of alcohol and centrifugation (50% propanol supernatant) | 178,000 | 113 |
| 4. | Resuspended pellet from 60% alcohol addition admixed in one volume of aqueous buffer | 140,500 | 89 |

In the second control procedure, n-propanol was added following centrifugation of the cell suspension. ATCC #31546 microbial cells (1.18 kg) were collected from a second bath of fermentation medium having the composition described in Procedure 1 above. A small sampling of cells was ruptured using the lysozyme solution of Procedure 1, and enzyme activity was measured by the GDH method of Procedure 2 above (Item 1 in Table III). The remaining cells were frozen at −15° C. for between 4 and 22 days. The frozen cells were placed in a 15-liter tank containing 11.8 liters of 0.1 M tris phosphate buffer, pH 7.5, and stirred vigorously at 4° C. for 48 hours. A 20-ml sample was removed, centrifuged, and enzyme activity of the supernatant was assayed as described in Procedure 2 above (Item 2 of Table III). The remaining cell suspension was centrifuged in a 2-liter capacity solids-holding centrifuge (Cepa type 41G) at 18,000 rpm at a flow rate of 15 liters/hour. The supernatant was collected. An equal volume of n-propanol at 4° C. was pumped into the vigorously mixing supernatant at a rate of 30 liters/hour. Upon completion, the alcohol suspension was pumped through a 2-liter capacity solids-holding centrifuge (Cepa type 41G), and the supernatant was collected. Enzyme activity of the supernatant was measured as described in Procedure 2 above (Item 3 of Table III). To the vigorously stirred 50% alcohol suspension, 5.75 liters of n-propanol at 4° C. was added. The resulting suspension was pumped through a 2-liter capacity solids-holding centrifuge (Cepa type 41G) at a rate of 60 liters/hour, and the solids were collected while the supernatant was discarded. The pellet was re-suspended in 0.3 liter of 0.1 M tris phosphate buffer, pH 7.5, and stirred overnight. The supernatant was collected by centrifugation in a refrigerated centrifuge at 17,000 rpm for 2 hours at 4° C., and enzyme activity of the supernatant was assayed as described in Procedure 2 above (Item 4 of Table III). Results of this control procedure are shown in Table III. A comparison of the two procedures shows that the overall enzyme yield is significantly increased (89% vs 35%) by the method of the present invention.

TABLE III

Summary of Purification Process with Addition of Alcohol Following Centrifugation of the Cell Suspension

| | Purification Step | Total Units | Yield % |
|---|---|---|---|
| 1. | An aliquot of the 1.18 kg of cells from the fermentation medium treated with lysozyme solution (initial activity) | 30,500 | |
| 2. | Enzyme released by stirring at 4° C. for 48 hours | 24,500 | 89 |
| 3. | Centrifugation, then addition of 50% alcohol (50% propanol supernatant) | 15,900 | 52 |
| 4. | Re-suspended pellet from 60% alcohol addition admixed in one volume of aqueous buffer | 10,700 | 35 |

Example 4

Stability Of Creatinine Iminohydrolase In Cell-Free Supernatant Achieved by Addition of Propanol Frozen cells of the aerobic soil microorganism ATCC #31546 were thawed and suspended in 10 liters of 0.1 M tris phosphate buffer, pH 7.5 per kg of cell wet weight as a 10% cell suspension. The suspension was vigorously stirred for 48 hours at 4° C. and then centrifuged in a refrigerated centrifuge at 39,000 xg for 10 minutes at 4° C. The enzyme-containing supernatant obtained was divided into two portions and maintained at 4° C. To one portion, an equal volume of n-propanol was added. Enzyme activity of each portion at 4, 8, 12, 16 and 20 hours was determined as described in Procedure 2 above.

The results showed that the enzyme remained stable in a 50% propanol solution for the duration of the test (20 hours), while that from the supernatant lacking propanol lost 50% of its activity after 12 hours and retained only about 30% of its activity after 20 hours.

The invention has been described in detail with particular reference to certain preferred embodiments thereof, but it will be understood that variations and modifications can be effected within the spirit and scope of the invention.

What is claimed is:

1. A method for the recovery of creatinine iminohydrolase enzyme produced by cells of an aerobic microorganism, comprising the steps of:
   (a) forming an aqueous suspension of said cells containing said enzyme;
   (b) disrupting said cells in said suspension to release said enzyme into said suspension;
   (c) before, during, or after step (b) and prior to removal of disrupted cells and other cellular components, introducing a water-miscible organic solvent into said suspension to form a mixture of said solvent and said suspension, the mixture being effective to retain said enzyme in the liquid phase thereof while undesired cellular components precipitate therefrom;
   (d) separating said enzyme-containing liquid phase of step (c) from said precipitate and said disrupted cells; and
   (e) introducing additional water-miscible organic solvent into said separated liquid phase of step (d) to precipitate the desired enzyme therefrom wherein said water-miscible solvent is selected from the group consisting of acetone, n-propanol and isopropanol.

2. The method as defined in claim 1 wherein step (b) is carried out by thawing frozen cells of said microorganism in said suspension while subjecting said suspension to agitation effective to maintain the suspension in a fluid state.

3. The method as defined in claim 1 wherein said enzyme-containing precipitate of step (e) is dissolved in an aqueous buffer composition to remove undesired water-insoluble components contained in said step (e) precipitate.

4. A method for the recovery of creatinine iminohydrolase enzyme produced by cells of the aerobic soil microorgaism ATCC #31546 comprising the steps of:
   (a) forming an aqueous suspension of said cells containing said enzyme;
   (b) disrupting said cells in said suspension to release said enzyme into said suspension;
   (c) before, during, or after step (b) and prior to removal of disrupted cells and other cellular components, introducing a water-miscible organic solvent into said suspension to form a mixture of said solvent and said suspension, the mixture being effective to retain said enzyme in the liquid phase thereof while undesired cellular components precipitate therefrom;
   (d) separating said enzyme-containing liquid phase of step (c) from said precipitate and said disrupted cells; and
   (e) introducing additional water-miscible organic solvent into said separated liquid phase of step (d) to precipitate the desired enzyme therefrom;
said steps (a)–(e) being carried out at a pH within the range of from about 5 to 10 wherein said water-miscible solvent is selected from the group consisting of acetone, n-propanol and isopropanol.

5. The invention as defined in claim 4 wherein step (b) is carried out by thawing frozen cells of said microorganism in said suspension while subjecting said suspension to agitation effective to maintain the suspension in a fluid state.

6. The invention as defined in claim 4 wherein said enzyme-containing precipitate of step (e) is dissolved in an aqueous buffer composition to remove undesired water-insoluble components contained in said step (e) precipitate.

7. The invention as defined in claim 4 wherein steps (c), (d) and (e) are carried out at a temperature within the range of from about $-10°$ to $37°$ C.

8. The invention as described in claim 4 wherein said water-miscible organic solvent in step (c) is selected from the group consisting of n-propanol, isopropanol, t-butanol and acetone.

9. The invention as described in claim 4 wherein said water-miscible organic solvent in step (c) and said additional solvent in step (e) is n-propanol.

10. The invention as described in claim 1 or 4 wherein said additional solvent in step (e) is n-propanol.

11. The invention as described in claim 1 or 4 wherein said additional solvent in step (e) is isopropanol.

12. The invention as described in claim 1 or 4 wherein said additional solvent in step (e) is acetone.

* * * * *